(12) United States Patent
Nigg et al.

(10) Patent No.: US 6,645,949 B1
(45) Date of Patent: Nov. 11, 2003

(54) TOXICITY OF BORON COMPOUNDS TO CERTAIN ARTHROPODS

(75) Inventors: Herbert N. Nigg, Lake Alfred, FL (US); Samuel E. Simpson, Lake Alfred, FL (US)

(73) Assignee: University of Florida, Gainesville, FL (US)

( * ) Notice: Subject to any disclaimer, the term of this patent is extended or adjusted under 35 U.S.C. 154(b) by 0 days.

(21) Appl. No.: 09/728,044

(22) Filed: Dec. 1, 2000

(51) Int. Cl.$^7$ .................. A01N 55/08; A01N 59/14
(52) U.S. Cl. .................. 514/64; 424/657; 424/658; 424/659; 424/660
(58) Field of Search ................ 424/657–660; 514/64

(56) References Cited

U.S. PATENT DOCUMENTS

| | | | |
|---|---|---|---|
| 4,332,609 A | | 6/1982 | Ott .................. 71/27 |
| 4,438,090 A | | 3/1984 | Brite .................. 424/10.31 |
| 4,537,773 A | * | 8/1985 | Shenvi .................. 514/63 |
| 4,617,188 A | | 10/1986 | Page et al. .................. 424/658 |
| 4,851,218 A | * | 7/1989 | Hildebrandt et al. .................. 424/84 |
| 4,873,084 A | | 10/1989 | Sallay .................. 424/658 |
| 4,988,511 A | | 1/1991 | Demetre .................. 424/84 |
| 5,314,699 A | | 5/1994 | Baden .................. 424/660 |
| 5,516,520 A | | 5/1996 | Yang et al. .................. 424/408 |
| 5,564,222 A | | 10/1996 | Brody .................. 43/124 |
| 5,587,221 A | | 12/1996 | McCamy et al. .................. 428/96 |
| 5,672,362 A | | 9/1997 | Burnett .................. 424/660 |
| 5,698,208 A | | 12/1997 | Nigg et al. .................. 424/405 |
| 5,871,780 A | * | 2/1999 | Moss .................. 424/659 |
| 5,928,634 A | * | 7/1999 | Uick et al. .................. 424/84 |
| 5,958,463 A | * | 9/1999 | Milne et al. .................. 424/660 |
| RE37,133 E | * | 4/2001 | Maynard .................. 556/7 |

FOREIGN PATENT DOCUMENTS

| | | | |
|---|---|---|---|
| FR | 2241252 | | 3/1975 |
| FR | 2707455 | * | 1/1995 |
| WO | 9107972 | | 6/1991 |

OTHER PUBLICATIONS

Chemical Abstracts 126:302615 (1997).*
Agricola Abstract 1998:787 (1998).*
Chemical Abstracts 133:306685 (Nov. 2000).*
Derwent abstract, accession No. 1995–062759, abstracting FR 2,707,455 (1995).*
Frear, Donald E. H. Chemistry of Insecticides, Fungicides and Herbicides. D. Van Nostrand Co., Inc., New York, 1948, p. 49.*
Chemical Abstracts 130:248320 (May 1999).*
Derwent abstract, accession No. 1995–231989, abstracting CN 1,087,783 (1994).*
Suomi et al. (1992), "Control of the Structure–Infesting Beetle, *Hemicoelus gibbicollis* (Coleopteran: Anobiidae) with Borates," *Journal of Economic Entomology* 8/92:1188–1193.
Grace et al. (1991), *Journal of Economic Entomology* 84(6):1753–1757.
Hagmann, L.E. (1982), "Ant Baits," *Pest Cont.* 50:30,32.
Rust (1986), Chapter 14, *Advances in Urban Pest Management*, Van Nostrand Reinhold Co., N.Y., pp. 350–351.
Klotz, J.H. et al. (2000), "Toxicity and Repellency of Borate–Sucrose Water Baits to Argentine Ants (Hymenopteran: Formicidae)," *J. Econ. Entomol.* 93:1256–1258.
Bare, O.S. (1945), "Boric Acid as a Stomach Poison for the German Cockroach," *J. Econ. Entomol.* 38:407.
Williams, D.F. et al. (2001), *American Entomol.* 47:146–159.
Terro Ant Killer product label (Date unavailable).
Terro Ant Killer II product label (Date unavailable).

* cited by examiner

*Primary Examiner*—John Pak
(74) *Attorney, Agent, or Firm*—Saliwanchik, Lloyd & Saliwanchik

(57) ABSTRACT

The present invention relates to materials and methods using boron compounds to control arthropods. Preferred target pests are insects of the orders Orthoptera (grasshoppers and crickets), Lepidoptera (moths and larvae), and Hymenoptera (preferably *Solenopsis invicta*, fire ants).

14 Claims, No Drawings

TOXICITY OF BORON COMPOUNDS TO CERTAIN ARTHROPODS

BACKGROUND OF THE INVENTION

Insects and other pests have plagued mankind for ages and cost farmers billions of dollars annually in crop losses and in efforts to keep these pests under control. The losses caused by pests in agricultural production environments include decreases in crop yields, reduced crop quality, and increased harvesting costs. Homeowners also expend significant funds in their efforts to control pests.

Synthetic chemical pesticides have provided effective methods of pest control. However, the public has become concerned about the amount of residual chemicals that might be found in food, ground water, and the environment. Stringent new restrictions on the use of pesticides and the elimination of some effective pesticides from the marketplace could limit economical and effective options for controlling destructive pests. Thus, there is an urgent need to identify pest control methods and compositions which are not harmful to the environment, that can be used in areas frequented by humans (especially children), and that can be used on food.

U.S. Pat. No. 4,873,084 relates to treating wood with ammoniumpentaborate and alkali metal and/or alkaline earth metals (sulfates, -sulfites and/or -hydrophosphates) as fire retardants, anti-smoldering agents, anti-fungal agents, and to control wood boring insects like termites and lyctid beetles. It is stated therein that ammonia and boric acid ($H_3BO_3$) are liberated from ammoniumpentaborate in the gut of wood decaying insects and that ammonia neutralizes the acidity of the content of the insect's gut, which inhibits the activity of cellulase enzyme (essential for the acid-catalyzed hydrolysis of cellulose to glucose in wood boring insects). It is also acknowledged therein that the liberation of boric acid from ammoniumpentaborate is significantly easier than from sodium borates, such as borax and diso-diumoctaborate. Boric acid is taught therein as being known to be toxic to certain insects. This reference also teaches the use of bariumtriborate, barium salts, or their calcium analogs, and ammonia containing bariumchloride or bariumhydroxide to react with ammoniumpentaborate (and disodiumoctaborate) to form active ingredients.

For further information regarding the use of borates to control a wood-destroying beetle, see Suomi et al, "Control of the Structure-Infesting Beetle, *Hemicoelus gibbicollis* (Coleoptera:Anobiidae) with Borates," *Journal of Economic Entomology*, August 1992, pp. 1188–1193.

U.S. Pat. No. 4,332,609 relates to a liquid fertilizer for plants that comprises a polyborate compound, which is formed by reacting a boric acid compound with an alkanolamine or an aliphatic polyamine. This patent does not relate to controlling insects and makes not even a suggestion of the sort.

WO 91/07972 relates to the use of carrageenan to form gelled baits and to make the baits attractive to certain insects such as roaches and (sweet-feeding) ants. It is stated therein that it is the carageenan component that causes insects to be attracted to the gelled bait for bait-ingesting purposes. It is indicated therein that the carageenan can be used to make baits containing many chemicals that are insecticidal sufficiently attractive to insects; chemicals such as boric acid, sodium borate, and many chemical insecticides are included as possibilities. In practical applications, the pH of these formulations appears to be too high for effective use against many pests.

Yang et al. in U.S. Pat. No. 5,516,520 teach the use of borax to convert pesticide mixtures into "rubbery masses" to provide controlled release formulations.

FR 2 241 252 discloses cockroach bait compositions containing boric acid or borax with a nutritive substance.

As referred to herein, cockroaches are considered to be of the Order Blattodea (also called Blattaria). Thus, as used herein, the Order Orthoptera excludes cockroaches and includes crickets (including mole crickets), grasshoppers, locusts, and katydids. This is consistent with, for example, *Common Names of Insects and Related Organisms*, Stoetzel, Entomological Society of America, 1989 (which is specifically incorporated by reference herein), and with more recent taxonomic systems.

Some taxonomic schemes classify cockroaches as being of the Order Dictyoptera and of the Suborder Blattodea (or Blattaria), with Mantodea (mantids) also being a Suborder of Dictyoptera. Accordingly, cockroaches are then considered to be of the Superfamily Blattoidea (with Blaberoidea being the other Superfamily of the Suborder Blattaria). While isopterans are sometimes also included as a Superfamily of Dictyoptera, it appears to be most consistent to classify isopterans separately from cockroaches and mantids.

U.S. Pat. No. 4,617,188 relates to borax and carob to control cockroaches. U.S. Pat. Nos. 4,988,511 and 4,438,090 relate to attempts to make boric acid compositions palatable to, or otherwise effective for controlling, cockroaches. U.S. Pat. No. 4,438,090 relates to a method of preparing an insecticide containing boric acid which comprises milling boric acid to a particle size between about 100 to about 400 mesh; blending the boric acid particles with magnesium stearate, silica gel, tricalcium phosphate, sucrose octa-acetate, or denatonium benzoate, and with a non-white powdered pigment, with the boric acid particles remaining smaller than about 100 mesh; and electrically charging the blend to induce an electrostatic charge on the discrete particles of the insecticide. Similarly, U.S. Pat. No. 4,988,511 relates to controlling cockroaches with an insecticidal paste composed of a delicately balanced mixture of sugar, milk solids, butter fat, water, and a green pigment of liquid food coloring with a powdered form of boric acid in 100 to 400 mesh.

Grace et al., *J. Econ. Entomol.*, 84(6):1753–1757 (1991) is concerned with the response of certain subterranean termites to borate dust and soil treatments. As referred to herein, termites are considered to be of the Order Isoptera. U.S. Pat. No. 5,564,222 relates to the use of cellulose bodies impregnated with borate salts for controlling termites.

Borax has also been used for treating carpets to control fleas (class Insecta, Order Siphonaptera). For example, there is a commercial product (a borate powder) available from FLEABUSTERS. See also U.S. Pat. No. 5,587,221, which relates to a carpet treatment for controlling fleas and mites (class Acari), but uses borax (a tetraborate) plus boric acid. U.S. Pat. No. 5,672,362 relates to the use of disodium octaborate tetrahydrate for controlling dust mites (Class Acari). U.S. Pat. No. 5,587,221 notes that octaborate is expensive to produce because obtaining octaborate requires the step and expense of driving off a certain amount of water. U.S. Pat. No. 5,314,699 is cited in U.S. Pat. No. 5,672,362 as disclosing the use of disodium octaborate tetrahydrate (more specifically, the use of the crystalline form thereof as a carpet treatment) for killing fleas, but U.S. Pat. No. 5,672,362, which relates to the control of mites, notes that it is commonly understood in the art that a chemical that is effective for controlling one type of pest is not necessarily effective for controlling another.

U.S. Pat. No. 5,698,208 is directed to the use of borax toxicants against fruit flies.

Notwithstanding the above, there is still a need in the art for improved toxicants that are effective against a broader range of pests, that have features for direct and easy application, and that are not environmental pollutants or potential carcinogens (or otherwise harmful to humans).

BRIEF SUMMARY OF THE INVENTION

The present invention relates to materials and methods of using boron compounds to control certain arthropods. Preferred target pests are insects of the Orders Orthoptera (grasshoppers and crickets), Lepidoptera (moths and larvae), and Hymenoptera (preferably Solenopsis invicta, fire ants).

DETAILED DESCRIPTION

The subject invention relates to the surprising observation that boron compounds are attractive to certain pests. In accordance with the subject invention, boron compounds, in effective amounts, can be used to kill pests directly and/or disrupt the oviposition of female target pests. It was especially surprising to find that boron compounds can be used to prevent female arthropods (as identified herein) from producing eggs.

Preferred target pests are insects of the Orders Orthoptera (including, as preferred target pests, grasshoppers and crickets), Lepidoptera (moths and larvae), and Hymenoptera (including, as preferred target pest, fire ants, e.g. Solenopsis invicta, which are of the Family Formicidae).

Control of the target pest can be a result of, for example, exposing a target pest to a bait/insecticidal composition so that the target pest ingests or otherwise contacts the composition. Control of the pest can take the form of killing the pest (immediately or prematurely), making the pest "sick" (to an adequate extent so that effective control of the pest is achieved), or interfering with (preventing or delaying) oviposition of female pests.

Boron compounds can be administered to pests in a variety of ways according to the subject invention. The boron compounds can be fed to the pests by placing or otherwise providing the boron compounds in areas frequented by the pests. Boron compounds administered in this manner are thus caused to contact the pests. The pests can be caused to contact and/or ingest the boron compound directly or indirectly by trophallaxis or by other contact with other pests that have directly contacted the administered boron compound. It is preferred (but not necessarily essential) for the target pests to ingest the boron compound.

While a preferred toxicant of the subject invention is borax (sodium borate decahydrate-10 mol $Na_2B_4O_7.10H_2O$ or sodium borate pentahydrate-5 mol $Na_2B_4O_7.5H_2O$), other suitable boron compounds may be utilized in effective amounts as substitutes for borax (or may be utilized in effective amounts in combination with borax or one another). Exemplary borate compounds of the present invention include anhydrous borax ($Na_2B_4O_7$), ammonium tetraborate (($NH_4)_2B_4O_7.4H_2O$), ammonium pentaborate (($NH_4)_2B_{10}O_{16}.8H_2O$), potassium pentaborate ($K_2B_{10}O_{16}.8H_2O$), potassium tetraborate ($K_2B_4O_7.4H_2O$), sodium metaborate ((8 mol) $Na_2B_2O_4.8H_2O$), sodium metaborate ((4 mol) $Na_2B_2O_4.4H_2O$), disodium tetraborate decahydrate ($Na_2B_4O_7.10H_2O$), disodium tetraborate pentahydrate ($Na_2B_4O_7.5H_2O$), and disodium octaborate tetrahydrate ($Na_2B_8O_{13}.4H_2O$). Thus, the terms "boron compounds" and "boron toxicant(s)" are used broadly herein and include collectively and/or individually boron salts, borax, and any other suitable borax-type compounds. One or more of the above-listed toxicants can be used alone and/or in combination according to the subject invention.

The boron compounds of the subject invention may be utilized in the anhydrous and/or hydrous forms. However, when the anhydrous forms are selected, it should be appreciated by those versed in this art that such compounds are typically more expensive and will generally convert to a hydrated form in water or moisture environments. It should also be appreciated by those versed in this art that mixtures of boron compounds may be utilized. The borax-type toxicant available in such mixtures should achieve the proper molarity to ensure that the objectives of the present invention are not defeated.

Although a variety of boron compounds can be used according to the subject invention, certain boron compounds are preferred. For example, boron compounds other than boric acid are preferred for use according to the subject invention. Boric acid has a higher toxicity to non-target organisms and is more irritating to humans than other boron compounds that can be used according to the subject invention. Thus, the subject invention provides numerous advantages over the compounds that the art previously taught were required to achieve adequate pest control. Boron compounds other than ammonium pentaborate and the like are also preferred; as discussed above, U.S. Pat. No. 4,873,084 reports that boric acid can be easily liberated from such compounds. For that matter, the subject invention is preferably used to control a target pest, as identified herein, that is other than a wood-boring insect pest, the gut of which can be disrupted by the ammonia that reportedly can be liberated from ammonium pentaborate. In addition, boron compounds other than octaborates such as disodium octaborate are preferred for reasons mentioned above. For example, octaborates such as disodium octaborate tetrahydrate are more expensive to produce.

In addition to boron salts such as sodium tetraborate or borax, preferred boron compounds for use according to the subject invention include organoborates. An example of preferred organoborates for use according to the subject invention include the polyborates of U.S. Pat. No. 4,332,609, entitled "Fertilizing Plants with Polyborates." It should be noted that while a wide range of application rates of the boron compound can be used according to the subject invention, preferred rates are much lower than those suggested by U.S. Pat. No. 4,322,609. As described therein, boric acid can be reacted with an alkanolamine or an aliphatic polyamine to form polyborate compounds. The organoborates for use according to the subject invention are not limited to those examples of polyborates. The subject organoborates include organic molecules that include a boron atom so long as they are suitable for use in accordance with the teachings of the subject invention (i.e., for administering to and controlling one or more of the target pests identified herein). Thus, a wide range of organic molecules (including aliphatic molecules, alkyl groups, and amines in addition to those exemplified in U.S. Pat. No. 4,332,609) can be reacted with boric acid, for example, to form organoborates for use according to the subject invention.

According to the subject invention, the boron compound(s) is the toxicant/active ingredient for pest control. In accordance with the present invention, the boron compounds may be utilized alone or in combination with suitable carriers, attractants, food sources, and/or with other insecticides and other toxicants. Thus, baits, agars, liquifiers, sweeteners, carriers, attractants (including pheromones and feeding/food source attractants), feeding stimulants, and the like can be used according to the subject invention.

While those versed in the relevant arts would understand that the compositions of the present invention may be applied by any suitable means, it would also be recognized that some carriers and the like are preferred over others. For example, carageenan can raise the pH of baits to levels that are not preferred and/or that are unacceptable. (Neutral pH ranges are preferred because some pests will avoid bait that has a pH that is too low or too high.) Thus, although it can be used, carageenan is not a preferred carrier/attractant.

Although baits, carriers, and attractants can be used to deliver boron compounds of the subject invention, it has been surprisingly determined that the boron compounds are sufficiently attractive to the target pests to be, advantageously, effective insecticides when used alone. Thus, attractants and the like are not necessary according to the subject invention; certain preferred embodiments of insecticidal compositions of the subject invention consist essentially of the boron compound(s).

Notwithstanding the foregoing, baits and carriers targeted for specific pests can also be used with the active ingredient (a boron compound) of the subject invention. For example, fire ants, lepidopterans (and subgroups thereof), and orthopterans (including grasshoppers and crickets) can be (but are not essentially) targeted in this manner.

Formulated bait granules optionally containing an attractant or other additive(s) can be applied to the environment of the target pest. The bait may be applied liberally since most compounds for use according to the subject invention are virtually nontoxic to animals and humans. The product may also be formulated as a spray or powder. The toxicant may also be incorporated into a bait or food source for the pest. Target pests can pick the product up on their feet or abdomen and carry it back to the nest where other pests will be exposed to the toxin.

Advantageously, boron compounds of the subject invention can be used in this manner as a slow-acting toxicant to achieve a delayed kill if an immediate kill is not desired. This is especially advantageous for killing entire colonies of social insects such as fire ants. By not causing an immediate kill, the foraging insects can gather the boron toxicant and distribute it to the entire colony before the boron toxicant causes death of the target insects.

As would be appreciated by a person skilled in the art, the pesticidal concentration will vary widely depending upon the particular end use and the nature of the particular formulation, especially whether it is a concentrate or to be used directly. The pesticide will typically be present in at least ½ to 1% by weight and may be 100% by weight. Dry formulations will typically have from about 1–95% by weight of the pesticide while the liquid formulations will generally be from about 1–60% by weight of the solids in the liquid phase. These formulations will typically be administered at about 50 mg (liquid or dry) to 1 kg or more per hectare in agricultural settings.

The formulations can be applied by spraying, dusting, sprinkling, baiting, or the like, to the environment of the pests. Depending on the type of pest being targeted, this would include, for example, agricultural fields and crops, outdoor settings, and in and/or around buildings.

Optionally, other toxicants (such as Malathion, Dibrom® and Naled®), may be used in combination with one or more of the boron compounds of the subject invention. However, any one of the boron compounds of the subject invention is sufficiently active so that it can be used in compositions consisting essentially of the boron compound as the active ingredient/toxicant.

In one embodiment, compositions of the subject invention include a mixture of boron compounds in an effective amount and, for example, protein hydrolysate bait or any synthetic bait to generate a bait or lure in the form of a patty, heavy cream, pellet, gel, foam, paste, liquid, or spray. An example of a patty in accordance with the present invention includes boron in an amount of between about 0.01M and about 0.1M or more, agar, yeast hydrosylate, sugar, and water. The bait or lure may also be in the free form or, alternatively, in a form, such as granules or tablets, agglomerated with or without the aid of a binder. Moreover, the bait or lure can be fixed or impregnated on a support or absorbed therein, and this support may include, for instance, agar, paper, cardboard, plastic such as polystyrene, polyvinyl chloride, polyvinyl acetate and cellulose acetate, glass, pumice, crushed marble, silica, and/or silica minerals. Attractants (such as Male Lure 11® and methyl eugenol), sweeteners, carriers, and/or liquefiers and the like may optionally be used in combination with the boron compound(s). The bait or lure may then be placed in selected locations such that the target pests are likely to encounter and ingest the boron toxicant to assure the desired effect, but preferably out of the way of normal human or animal traffic.

Compositions of the subject application can also be administered with pressurized applications, hydraulic oil squirt cans, and aerial sprays. Moreover, it should be appreciated by those skilled in this art that weather conditions should be taken into account whenever the compositions of the present invention are to be applied. For instance, treatment or retreatment are not preferred if weather reports indicate a 50% or greater chance of precipitation within 48 hours.

In accordance with the present invention, the methods and compositions are safe and effective and, therefore, can be used on any surface, such as paper, cardboard, concrete, plastic, metal, glass, and plants, and at any location, such as any outdoor location, and in and around buildings. In addition, the compositions of the present invention can be easily applied directly to areas of infestation and will remain active for extended periods of time. Therefore, the boron compounds of the present invention may be used in residential preparations, commercial crop production, eradication programs, and suppression programs for pests identified herein.

One objective of the present invention is in wide-area suppression and eradication programs. Currently, hard pesticides such as malathion are formulated with a protein hydrolysate bait, such as Miller's Nu-Lure®. The protein hydrolysates are usually corn-based. Instead of the hard pesticide, one of the boron compounds detailed herein may be substituted. This substitution can result in a pH change from about 5.0 to 8.5, and a precipitate can form, which is filtered to prevent clogging the spray nozzles of either ground or air application equipment. The protein hydrolysate may be used full-strength or diluted to about 10% with water before the boron compound is added. The final proteinaceous bait spray may be used over wide inhabited areas.

Boron toxicants of this invention can also be formulated with an extender or gel, such as Min-U-Gel®, Thixcin E®, Myverol® and CAB-O-SIL®. These are commercially available. In this case, the precipitate is not a concern because gels are typically sprayed in a solid stream. The gels can be formulated with synthetic bait and/or natural proteinaceous baits. This method of application reduces worker and public inconvenience of aerial spraying of large areas. Thus, gel formulations and/or the liquid formulations can be used.

For lethal concentrations to reduce a pest population at a targeted area, a boron compound of the present invention is preferably applied about once per week for at least six weeks (7 days per week). For lower concentrations which suppress egg production, a weekly application schedule for six weeks (7 days per week) is preferred. These schedules are based on a pest life-span of about 40 days in the field and egg production suppression of at least 7 days. In a limited geographical area, these schedules should be capable of suppressing pest populations below economic levels. With wider geographical use, large target pest populations can also be eradicated.

In accordance with the present invention, a preferred range of effective molarities for the boron toxicant is in the range of between about 0.02M and about 0.12M or higher. It is preferred that the pest ingests between about 5 micromoles and about 10 micromoles of a boron compound during about a 24 hour period of time. If the objective is to prevent or stop the females from laying eggs for about seven days or more, it is preferred that the pest ingests between about 2.5 micromoles and about 5.0 micromoles of boron during about a 24 hour period of time.

It should therefore now be understood by those versed in this art that the novel methods and compositions of the present invention provide a simple yet unique solution to controlling certain pest populations by providing a toxicant that is surprisingly found to also be an attractant. More particularly, it has been surprisingly discovered that the methods and compositions of the present invention uniquely attract these pests and cause these pests to stay and engorge, so that the objectives of the present invention are accomplished, i.e., controlling the pest population by either killing or inhibiting the pest directly, or by preventing the female pests from producing eggs. Using the present invention to suppress egg production breaks the life cycle of the target pest. Compositions of the subject invention lack adverse environmental effects and enhance worker safety. Moreover, the present invention is adaptable to integrated pest management programs.

All patents, patent applications, provisional applications, and publications referred to or cited herein are incorporated by reference in their entirety to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

EXAMPLE 1

Control of *Scapteriscus abbreviatus* (Mole Crickets)

All crickets used for this test were laboratory-reared *Scapteriscus abbreviatus*. On day one, twenty female crickets were placed in individual 3" diameter open-end containers filled with 16 ounces of soil and having a petri dish cover on each end. Ten female mole crickets were fed $\frac{1}{16}$ tsp. of bait, and ten females were fed $\frac{1}{16}$ tsp. of cricket chow. The bait was cricket chow formulated to contain 5% sodium tetraborate, weight:weight (w/w). On day 4, each of the virgin crickets received a second respective feeding. Three days later, each female was given cricket chow placed in each container.

On day 45, none of the female crickets that fed upon the bait were alive. All of the control group (given cricket chow only) were alive.

EXAMPLE 2

Comparison of the Survival Rate of Male Compared to Female *Scapteriscus abbreviatus*

All mole crickets used for this test were laboratory reared *Scapteriscus abbreviatus*. On day one, twenty males and twenty females were placed in individual 20 dram vials of soil. Ten male and ten female mole crickets were each given $\frac{1}{16}$ tsp. of bait, and another group of ten males and ten females were each given $\frac{1}{16}$ tsp. of cricket chow. The bait was cricket chow formulated to contain 5% sodium tetraborate, weight:weight (w/w). Four days later, each mole cricket received the same respective treatments.

All mole crickets were alive on day seven, and all were given cricket chow. On day eleven, six female and six male mole crickets that had fed upon the boron-salt bait were dead, and four female and four male were moribund. All mole crickets that received only the cricket chow were alive.

Thus, no difference was observed between male and female mole cricket survival rates after ingesting bait.

EXAMPLE 3

Further Testing for Control of *Scapteriscus abbreviatus*

All mole crickets used for this trial were laboratory reared *Scapteriscus abbreviatus*. On day one, thirty males and thirty females were placed in individual 20 dram vials of soil. Ten male and ten female mole crickets were each given $\frac{1}{16}$ tsp. of Bait A as prepared in Examples 1 and 2. Another group of ten males and ten females were given $\frac{1}{16}$ tsp. of Bait B (10% w/w sodium tetraborate) and another group of ten male and ten female crickets were each given $\frac{1}{16}$ tsp. of cricket chow. Four days later, each cricket received their respective diet. One male of the Bait B group and all of the Bait A group and cricket chow diet-fed mole crickets were alive. On day seven, all surviving crickets (nineteen Bait A, one Bait B, and all control group) were given cricket chow. On day eleven, only the *Scapteriscus abbreviatus* fed only with untreated cricket chow survived the trial. See Table 1.

TABLE 1

|  | Live | Dead |
|---|---|---|
| Bait A | 0 | 20 |
| Bait B | 0 | 20 |
| Cricket Chow (only) | 20 | 0 |

EXAMPLE 4

Control of *Solenopsis invicta* (Imported Fire Ants)

Bait was prepared to include 5% sodium tetraborate, weight:weight, by first weighing out 397 g of bait and 19.85 g of sodium tetraborate. These ingredients were placed into a plastic bag and shaken for three minutes. The total was 416.85 g of material. This material was divided into 100 g aliquots.

Fire ant mounds that were tested were all well-established and had raised soil mounds of >18" in diameter. The mounds selected for testing were at least 50' from the center mound. Treatments were as indicated in Table 2; all treatments were random.

A 48"×⅛" dowel rod was inserted to 6" into each test mound. The dowel was removed after 30 seconds. The number of ants adhering to the stick was estimated. Tests were conducted in the evening (4:30 p.m.–7:30 p.m.) with air temperatures between about 80° F. to about 90° F.

The following results show that boron compounds can be used to control imported fire ants.

Treatment schedules were as follows:

TABLE 2

| Treatment # | Treatment | n |
|---|---|---|
| 1 | Bait + borax 5% | 4 |
| 2 | Bait only | 4 |
| 3 | Control | 4 |

TABLE 3

Estimated Number of Ants Observed

| | Replication | | | |
|---|---|---|---|---|
| Treatment # | 1 | 2 | 3 | 4 |
| Day 1. | | | | |
| 1 | 50+ | 50+ | 50+ | 30–50 |
| 2 | 50+ | 30–50 | 50+ | 50+ |
| 3 | 50+ | 50+ | 50+ | 50+ |
| Day 7. | | | | |
| 1 | 10–30 | 30–50 | 30–50 | 30–50 |
| 2 | 50+ | 30–50 | 50+ | 30–50 |
| 3 | 50+ | 50+ | 50+ | 50+ |
| Day 15. | | | | |
| 1 | 10–30 | <10 | <10 | 10–30 |
| 2 | 50+ | 50+ | 50+ | 30–50 |
| 3 | 50+ | 50+ | 30–50 | 50+ |
| Day 22. | | | | |
| 1 | 0 | 0 | <10 | 0 |
| 2 | 50+ | 50+ | 30–50 | 50+ |
| 3 | 50+ | 50+ | 30–50 | 50+ |
| Day 30. | | | | |
| 1 | 0 | 0 | 0 | 0 |
| 2 | 50+ | 50+ | 30–50 | 50+ |
| 3 | 50+ | 50+ | 50+ | 50+ |

EXAMPLE 5

Control of Diamond Back Moth (DBM; *Plutella xylostella*) and Inhibition of Egg Deposition On day one, six cages (24" cube) were set up with five virgin DBM females and five virgin DBM males, one cabbage seedling, and one sugar pad (10% sucrose) in each cage. The sugar solution in three cages also contained 4% sodium tetraborate (4 g+96 ml, w:v water). The virgin adult DBM were obtained by isolating colony pupae individually in vials two days prior. The adults emerged one day prior to day one and on day one. They were provided a 10% sugar solution with or without sodium tetraborate, as soon as they emerged, by placing the vials with cloth bottoms on cotton pads.

The cages were placed in environmental rooms where the temperature was 25–26° C. and the day length was 14 hours.

Sugar pads were a single layer of rolled cotton approximately 8 cm square. Each pad was soaked in the appropriate solution, placed in the bottom of a petri dish (95×15 mm), and the excess water was pressed out. Each pad held about 30 ml of solution.

The cabbage seedlings were in Descn. No. 12 plastic pots. The surface of the soil was covered with a thin layer of Plaster of Paris.

On each of days two, three, four, five, and six, the sugar pads and plants were changed (once) between 1:00 p.m. and 5:00 p.m.

Results are reported in Tables 4 and 5.

TABLE 4

Eggs, larvae and % egg hatch in control and sodium tetraborate fed *P. xylostella*.

| | Sugar | | | | Sodium tetraborate | | | |
|---|---|---|---|---|---|---|---|---|
| | 1 | 2 | 3 | Total | 1 | 2 | 3 | Total |
| | Number of Eggs | | | | | | | |
| Day 2 | 16 | 184 | 102 | 302 | 44 | 110 | 48 | 202 |
| Day 3 | 7 | 90 | 302 | 399 | 266 | 124 | 109 | 499 |
| Day 4 | 246 | 134 | 103 | 483 | 61 | 23 | 101 | 185 |
| Day 5 | 107 | 28 | 80 | 215 | 17 | 4 | 98 | 119 |
| Day 6 | 127 | 64 | 88 | 279 | 30 | 0 | 28 | 58 |
| Day 7 | 71 | 41 | 74 | 186 | 1 | 0 | 0 | 1 |
| Total | 574 | 541 | 749 | 1864 | 419 | 261 | 384 | 1064 |
| Average | | | | 621.3 | | | | 354.7 |
| % of sugar | | | | | | | | 57.1 |
| | Number of Larvae | | | | | | | |
| Day 2 | 7 | 92 | 58 | 157 | 18 | 64 | 17 | 99 |
| Day 3 | 7 | 70 | 175 | 252 | 196 | 92 | 100 | 388 |
| Day 4 | 153 | 103 | 72 | 328 | 29 | 12 | 72 | 113 |
| Day 5 | 75 | 17 | 46 | 138 | 4 | 3 | 63 | 70 |
| Day 6 | 83 | 25 | 21 | 129 | 8 | 0 | 28 | 36 |
| Day 7 | 40 | 13 | 43 | 96 | 0 | 0 | 0 | 0 |
| Total | 365 | 320 | 415 | 1100 | 255 | 171 | 280 | 706 |
| Average | | | | 366.7 | | | | 235.3 |
| % of sugar | | | | | | | | 64.2 |
| | Percent Hatch | | | | | | | |
| Day 2 | 43.8 | 50.0 | 56.9 | 50.2 | 40.9 | 58.2 | 35.4 | 44.8 |
| Day 3 | 100.0 | 77.8 | 57.9 | 78.6 | 73.7 | 74.2 | 91.7 | 79.9 |
| Day 4 | 62.2 | 76.9 | 69.9 | 69.7 | 47.5 | 52.2 | 71.3 | 57.0 |
| Day 5 | 70.1 | 60.7 | 57.5 | 62.8 | 23.5 | 75.0 | 64.3 | 54.3 |
| Day 6 | 65.4 | 39.1 | 23.9 | 42.8 | 26.7 | | 100.0 | 63.3 |
| Day 7 | 56.3 | 31.7 | 58.1 | 48.7 | 0.0 | | | 0.0 |
| Total | 63.6 | 59.1 | 55.4 | | 60.9 | 65.5 | 72.9 | |
| Average | | | | 59.4 | | | | 66.4 |

TABLE 5

Mortality of sodium tetraborate fed (and control) *P. xylostella*.

| | Sugar | | | | Sodium tetraborate | | | |
|---|---|---|---|---|---|---|---|---|
| | 1 | 2 | 3 | Total | 1 | 2 | 3 | Total |
| | Number of Dead Males | | | | | | | |
| Day 2 | 0 | 0 | 0 | 0 | 0 | 0 | 0 | 0 |
| Day 3 | 0 | 0 | 0 | 0 | 0 | 0 | 0 | 0 |
| Day 4 | 0 | 0 | 0 | 0 | 0 | 0 | 0 | 0 |
| Day 5 | 0 | 0 | 0 | 0 | 0 | 1 | 1 | 2 |

TABLE 5-continued

Mortality of sodium tetraborate fed (and control) *P. xylostella.*

| | Sugar | | | | Sodium tetraborate | | | |
|---|---|---|---|---|---|---|---|---|
| | 1 | 2 | 3 | Total | 1 | 2 | 3 | Total |
| Day 6 | 0 | 0 | 0 | 0 | 2 | 0 | 2 | 4 |
| Day 7 | 0 | 0 | 0 | 0 | 2 | 2 | 1 | 4 |
| Number of Live Males | | | | | | | | |
| Day 7 | 5 | 4 | 5 | 14 | 1 | 0 | 1 | 2 |
| Number of Dead Females | | | | | | | | |
| Day 2 | 0 | 0 | 0 | 0 | 0 | 0 | 0 | 0 |
| Day 3 | 0 | 0 | 0 | 0 | 0 | 1 | 0 | 1 |
| Day 4 | 1 | 1 | 0 | 2 | 0 | 1 | 0 | 1 |
| Day 5 | 0 | 0 | 0 | 0 | 0 | 1 | 0 | 1 |
| Day 6 | 0 | 0 | 0 | 0 | 1 | 1 | 1 | 3 |
| Day 7 | 0 | 0 | 0 | 0 | 3 | 0 | 3 | 6 |
| Number of Live Females | | | | | | | | |
| Day 7 | 4 | 4 | 5 | 13 | 1 | 0 | 1 | 2 |

Based on the foregoing, it was concluded that the boron compound (in 10% sucrose) killed males and females of *P. xylostella*. In surviving females there was delay/cessation of egg deposition.

It should be understood that the examples and embodiments described herein are for illustrative purposes only and that various modifications or changes in light thereof will be suggested to persons skilled in the art and are to be included within the spirit and purview of this application and the appended claims.

What is claimed is:

1. A method of controlling mole crickets wherein said method comprises feeding said mole crickets an insecticidal composition comprising an effective amount of a borate compound.

2. The method of claim 1 wherein said borate compound is an organoborate.

3. The method of claim 1 wherein said borate compound is borax.

4. The method of claim 1 wherein said insecticidal composition consists essentially of said borate compound.

5. The method of claim 4 wherein said borate compound is an organoborate.

6. The method of claim 4 wherein said borate compound is borax.

7. A method of controlling fire ants wherein said method comprises feeding said fire ants an insecticidal composition comprising an effective amount of a borate compound, and wherein said borate compound is present in said composition at a concentration that is at least 1% by weight.

8. The method of claim 7 wherein said borate compound is an organoborate.

9. The method of claim 7 wherein said borate compound is borax.

10. The method of claim 7 wherein said insecticidal composition consists essentially of said borate compound.

11. The method of claim 10 wherein said borate compound is an organoborate.

12. The method of claim 10 wherein said borate compound is borax.

13. The method of claim 7 wherein said borate compound is present in said composition at a concentration of about 5% or less by weight.

14. The method of claim 10 wherein said borate compound is present in said composition at a concentration of about 5% or less by weight.

* * * * *

UNITED STATES PATENT AND TRADEMARK OFFICE
CERTIFICATE OF CORRECTION

PATENT NO. : 6,645,949 B1
DATED : November 11, 2003
INVENTOR(S) : Herbert N. Nigg and Samuel E. Simpson It is certified that error appears in the above-identified patent and that said Letters Patent is hereby corrected as shown below:

Column 2,
Line 56, "plus" should read -- plus --.

Column 3,
Lines 54 and 66, "$Na_2 B_4O_7.10H_2O$" should read -- $Na_2 B_4O_7 \bullet 10H_2O$ --.
Lines 55 and 67, "$Na_2 B_4O_7.5H_2O$" should read -- $Na_2 B_4O_7 \bullet 5H_2O$ --.
Line 61, "$(NH_4)_2B_4O_7.4H_2O$" should read -- $(NH_4)_2B_4O_7 \bullet 4H_2O$ --.
Line 62, "$(NH_4)_2B_{10}O_{16}.8H_2O$" should read -- $(NH_4)_2B_{10}O_{16} \bullet 8H_2O$ --.
Line 63, "$K_2B_{10}O_{16}.8H_2O$" should read -- $K_2 B_{10}O_{16} \bullet 8H_2O$ --
Line 63, "$K_2B_4O_7.4H_2O$" should read -- $K_2B_4O_7 \bullet 4H_2O$ --.
Line 64, "(8 mol) $Na_2 B_2O_4.8H_2O$" should read -- (8 mol) $Na_2 B_2O_4 \bullet 8H_2O$ --.
Line 65, "(4 mol) $Na_2 B_2O_4.8H_2O$" should read -- (4 mol) $Na_2 B_2O_4 \bullet 4H_2O$ --.

Column 4,
Line 1, "$Na_2 B_8O_{13}.4H_2O$" should read -- $Na_2 B_8O_{13} \bullet 5H_2O$ --.

Signed and Sealed this

Fourteenth Day of September, 2004

JON W. DUDAS
*Director of the United States Patent and Trademark Office*